(12) United States Patent
Minton

(10) Patent No.: US 6,969,607 B2
(45) Date of Patent: *Nov. 29, 2005

(54) LOCKABLE PETRI DISH

(75) Inventor: Kenneth L. Minton, West Linn, OR (US)

(73) Assignee: PML Microbiologicals, Inc., Wilsonville, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/861,984

(22) Filed: Jun. 4, 2004

(65) Prior Publication Data
US 2005/0089997 A1 Apr. 28, 2005

Related U.S. Application Data

(63) Continuation-in-part of application No. 10/695,066, filed on Oct. 27, 2003, now abandoned.

(51) Int. Cl.[7] ............................................. C12M 1/34
(52) U.S. Cl. ............... 435/288.3; 435/288; 435/305.3; 435/305.4; 435/309.4

(58) Field of Search ..................... 422/102; 435/288.3, 435/288.4, 288.5, 305.1, 305.2, 305.3, 305.4, 435/309.4; 220/288, 293; 215/211, 214, 215/329

(56) References Cited

U.S. PATENT DOCUMENTS

| | | | | |
|---|---|---|---|---|
| 4,634,676 A | * | 1/1987 | Sapatino | 435/309.4 |
| 5,638,976 A | * | 6/1997 | Arnold | 220/298 |
| 5,695,988 A | * | 12/1997 | Chong | 435/305.1 |
| 6,602,704 B1 | * | 8/2003 | Maxwell et al. | 435/305.4 |

* cited by examiner

Primary Examiner—David Redding
(74) Attorney, Agent, or Firm—Chernoff, Vilahuer, McClung & Stenzel, LLP

(57) ABSTRACT

A lockable Petri dish is disclosed wherein the lid and base of the dish are provided with at least two pairs of locking members, each comprising a radial sheath and a sheath-engaging tab.

9 Claims, 3 Drawing Sheets

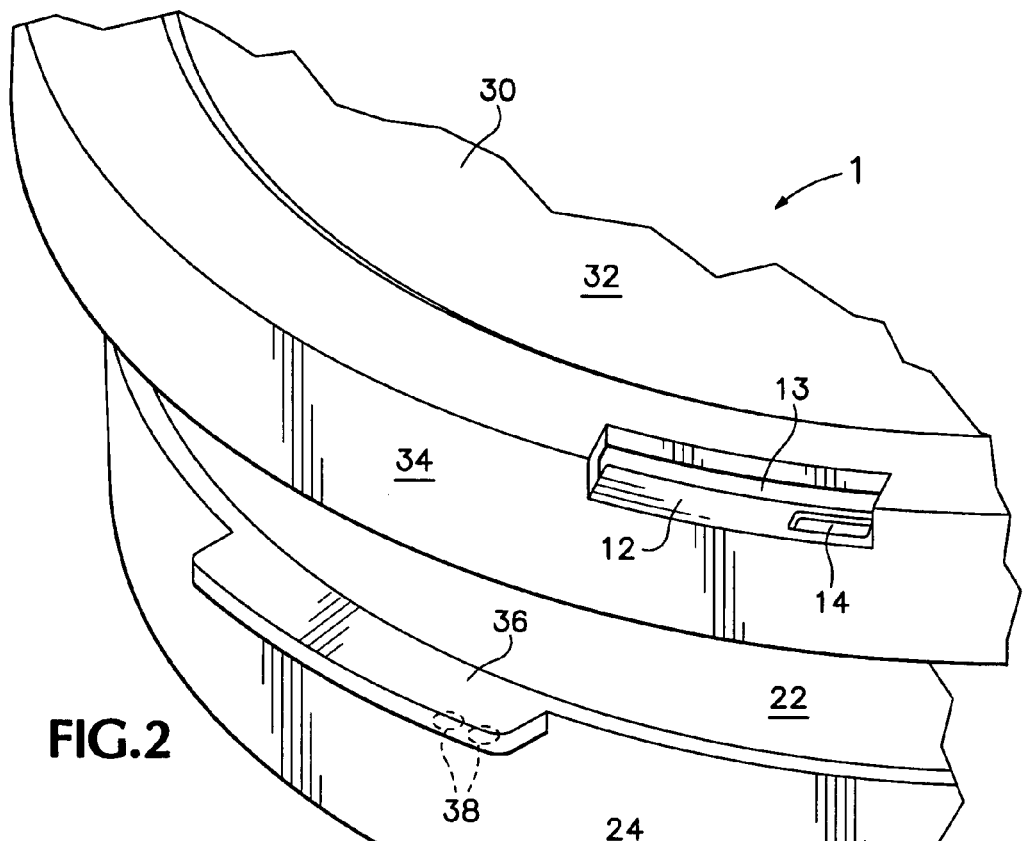
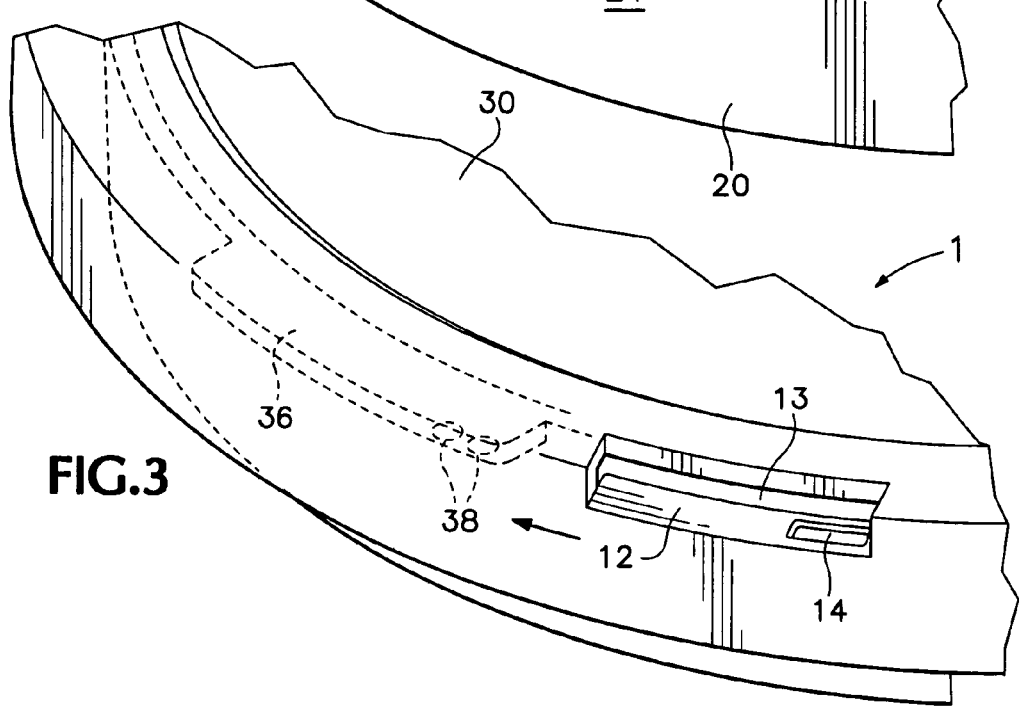

LOCKABLE PETRI DISH

This is a continuation-in-part of Ser. No. 10/695,066 filed Oct. 27, 2003, now abandoned, the priority of which is claimed pursuant to 35 USC §120.

BACKGROUND OF THE INVENTION

The use of Petri dishes for growing colonies of microorganisms such as bacteria or fungi is well known. A Petri dish typically comprises a short cylindrical open dish for holding microorganism growth medium and an overlapping cylindrical cover that isolates the growth medium and microorganisms from the external environment. Petri dish covers may be loosely fitting so that the seal and the dish arises simply from the weight of the cover bearing upon the cylindrical side walls of the dish. Petri dish covers may also be tightly securable to and detachable from the dish, which facilitates lifting the Petri dish by its cover.

One such design is disclosed in U.S. Pat. No. 3,769,936, wherein the cover may be secured to the dish by ribs in the side walls of the cover that resiliently contact the side walls of the dish so as to form a compression fit. However, this design has the inherent drawback that the compression fit is often either too tight to allow ready disengagement between the cover and dish or too loose, which can lead to accidental spillage or contamination when handling the Petri dish.

What is needed therefore is a lockable Petri dish that does not lock except upon application of a specific intentionally applied force, that provides a secure locking engagement between the cover and the dish, and which may be readily disengaged from the locking engagement. These needs are met by the present invention, which is summarized and described in detail below.

BRIEF SUMMARY OF THE INVENTION

The present invention comprises a lockable Petri dish wherein the cover and dish components of the Petri dish are prevented from premature or accidental locking engagement with each other so as to permit rapid pre-loading with growth medium, yet are readily lockable and unlockable from each other.

BRIEF DESCRIPTION OF THE SEVERAL VIEWS OF THE DRAWINGS

FIG. 2 is a close-up view of FIG. 1.

FIG. 3 is a partial perspective view of FIG. 1 showing alignment of exemplary locking elements of the invention.

DETAILED DESCRIPTION OF PREFERRED EMBODIMENTS

Figure 1:
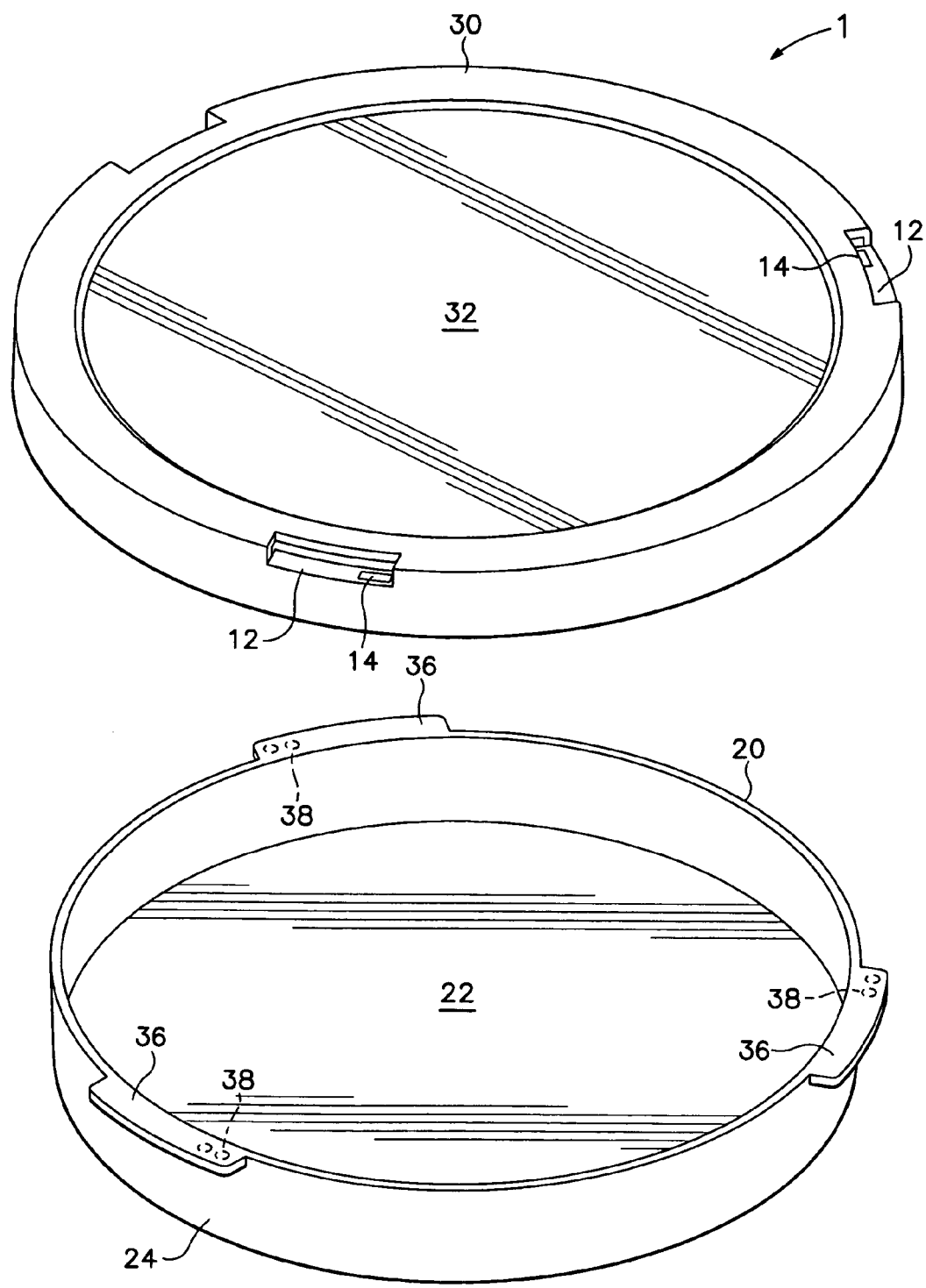
FIG. 1 is an exploded perspective view of an exemplary embodiment of the Petri dish of the invention.
Figure 4:
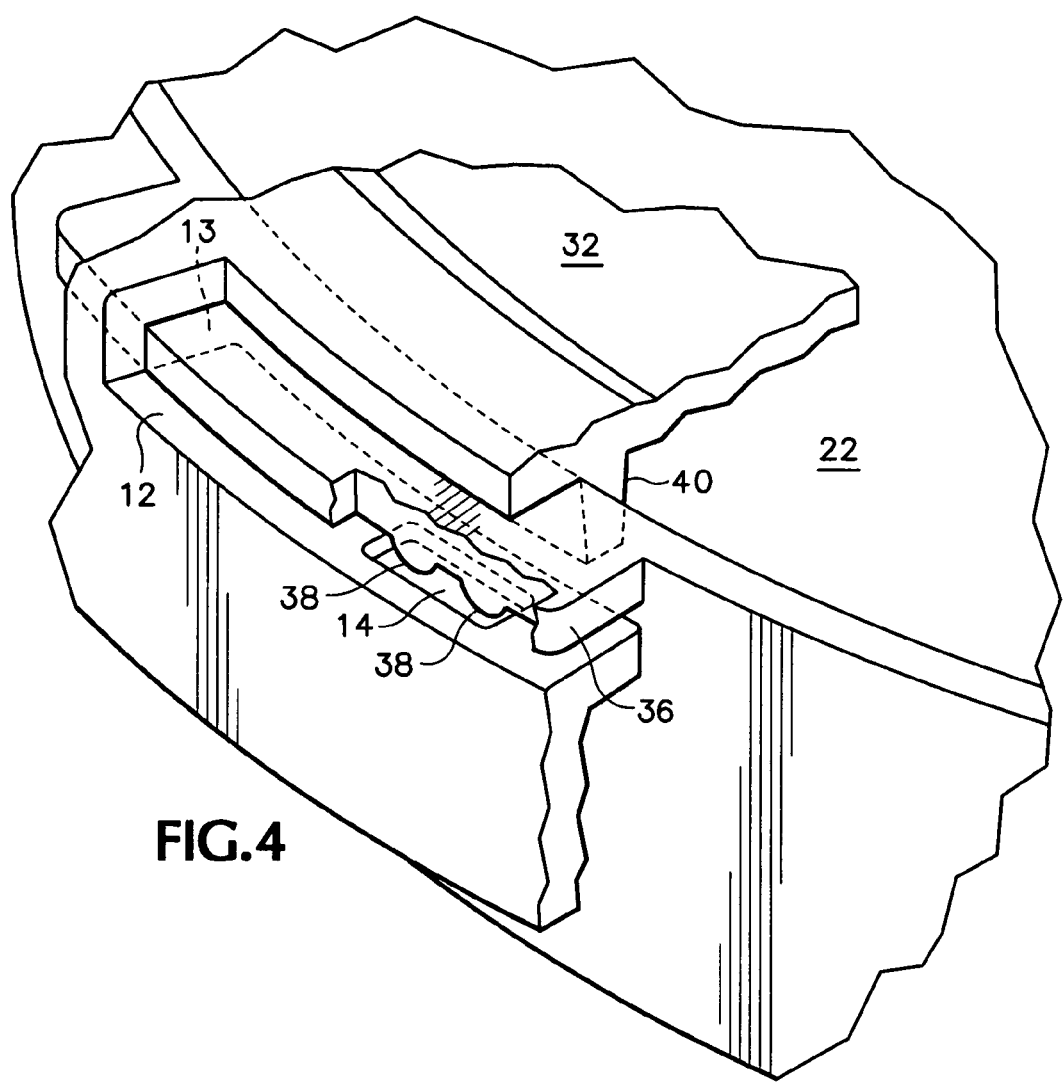
FIG. 4 is a partial perspective view of FIG. 3 with a cutaway view of one of the locking elements.

Referring to the drawings, wherein the same numerals refer to like elements, there is shown in FIGS. 1–4 a Petri dish 1 comprising a circular dish 20, dish 20 consisting of a flat bottom plate 22 and a bottom cylindrical sidewall 24. The Petri dish further comprises a circular lid 30, consisting of a lid top plate 32 and a top cylindrical side wall 34. Lid 30 is preferably transparent so as to permit viewing of any microorganism growth.

Dish 20 and lid 30 are provided with locking means for securing the base and lid in locking engagement. The locking means comprises at least two pairs of locking members radially spaced apart from each other, preferably equidistantly, wherein each pair of locking members comprises sheath and tab members adapted to slidably engage with each other. More specifically, radial sheath 12 is preferably integral with lid 30 and has a sheath entry 13; the external radius of radial sheath 12 preferably corresponds to the external radius of lid 30. Bottom cylindrical side wall 24 of dish 20 is provided with an elongate radial tab 36 that is preferably integral with side wall 24, and is sized and shaped so as to be slidably engagable with sheath 12; the external radius of tab 36 preferably is slightly less than that of the external radius of lid 30. Although sheath 12 and tab 36 are preferred to be integral with lid 30 and dish 20, respectively, it should be understood that this arrangement could be reversed and still yield the desired locking means of the invention.

Lid 30 may be provided with an optional inner flange 40 so as to form a seal between lid 30 and dish 20 when the lid and dish are not in locking engagement.

It is often advantageous to pre-load dish 20 with a growth medium such as agar or a gel containing microorganism-specific nutrients or indicators, then assemble the base and lid components, seal them in sterile packaging and ship them to the laboratory or other end user. Such pre-loading and prepackaging is typically conducted on an automated basis, assembly-line style, with the lids rapidly being removed and replaced on the bases by a mechanical arm immediately before and after the agar or gel pour. For speed and efficiency, it is best that, immediately before and after the agar or gel loading, the lid not enter into locking engagement with the base as this tends to interfere with and so slow the automated pre-loading process. To prevent premature locking engagement between dish 20 and lid 30 on such an assembly line, tab 36 is provided on its lower side with at least one button-like protrusion 38 that prevents entry of tab 36 into sheath entry 13 absent application of a torquing force. Although protrusion(s) 38 are shown as being generally hemispherical in shape, it should be understood that virtually any shape of protrusion would function as well, including oval and rectangular. When sheath 12 is provided on the inner portion of its outer wall with at least one indent 14 sized and shaped so as to fit snugly with protrusion(s) 38 upon application of a torquing force such as would be caused by rotating lid 30 relative to dish 20 (schematically shown by the directional arrow in FIG. 3), protrusion(s) 38 also serve to securely lock lid 30 to dish 20, thereby permitting the Petri dish to be lifted and handled by grasping lid 30 without risk of accidental removal of the lid from the base. Although indent 14 is shown as being generally rectangular in shape in the drawings, it is to be understood that virtually any shape that accommodates protrusion(s) 38 would function as well, including oval and circular.

Preferably tab 36, protrusion(s) 38 and sheath 12 are all fabricated from a polymeric material having a slight degree of resiliency, so that when tab 36 enters sheath 12, those elements both resiliently yield until protrusion(s) 38 are in alignment with indent 14, whereupon they enter into locking engagement. A preferable polymeric material is polystyrene. The same resiliency of sheath 12, tab 36 and protrusion(s) 38 permits lid 30 to be readily disengaged from dish 20 by simply rotating the lid in an opposite direction relative to the dish. Preferably, to prevent tab 36 from passing all the way through sheath 12, the sheath is provided with an end wall 16 distal to sheath entry 13.

The Petri dish of the invention containing growth medium is preferably manufactured in an unlocked arrangement with the leading edge of tab 36 juxtaposed to entry 13 of tab 12, and is packaged for shipment to the end user in gas-impermeable sterile packaging.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A Petri dish comprising
   (a) a circular dish supported on a circular base, said dish having a bottom plate and a bottom cylindrical side wall, and
   (b) a circular lid having a top plate and a top cylindrical side wall, said lid sized so as to fit over bottom cylindrical side wall of said dish wherein said base and said lid are provided with locking means for securing said base and said lid in locking engagement, said locking means comprising at least two pairs of locking members, each of said pairs of locking members comprising (i) a radial sheath having an entry, and (ii) an elongate radial tab sized and shaped so as to be slidably engagable with said radial sheath and wherein said sheath is integral with said lid and said tab is integral with said bottom cylindrical side wall;

and wherein said radial tab has at least one protrusion and said radial sheath has at least one indent, with said protrusion and said indent being sized and located so as matingly engage each other:

and wherein said at least one protrusion is proximal to the entry of said sheath and said at least one indent is distal to the entry of said sheath.

2. The Petri dish of claim 1 wherein said tab has two protrusions.

3. The Petri dish of claim 2 wherein said sheath and said tab are slidably engagable with each other by rotating said lid relative to said base.

4. The Petri dish of claim 3 wherein said sheath and said tab are slidably disengagable from each other by rotating said lid relative to said base.

5. The Petri dish of claim 1 wherein said sheath has a closed end distal to said entry.

6. The Petri dish of claim 5 wherein said lid is transparent.

7. The Petri dish of claim 1 wherein said lid has an inner circumferential flange engageable with said bottom cylindrical side wall of said dish.

8. The Petri dish of claim 1 wherein said dish contains microorganism growth medium.

9. The Petri dish of claim 8 packaged in sterile packaging.

* * * * *